May 2, 1961 C. CAMPRUBI Plant Pat. 2,055
ROSE PLANT
Filed June 9, 1960
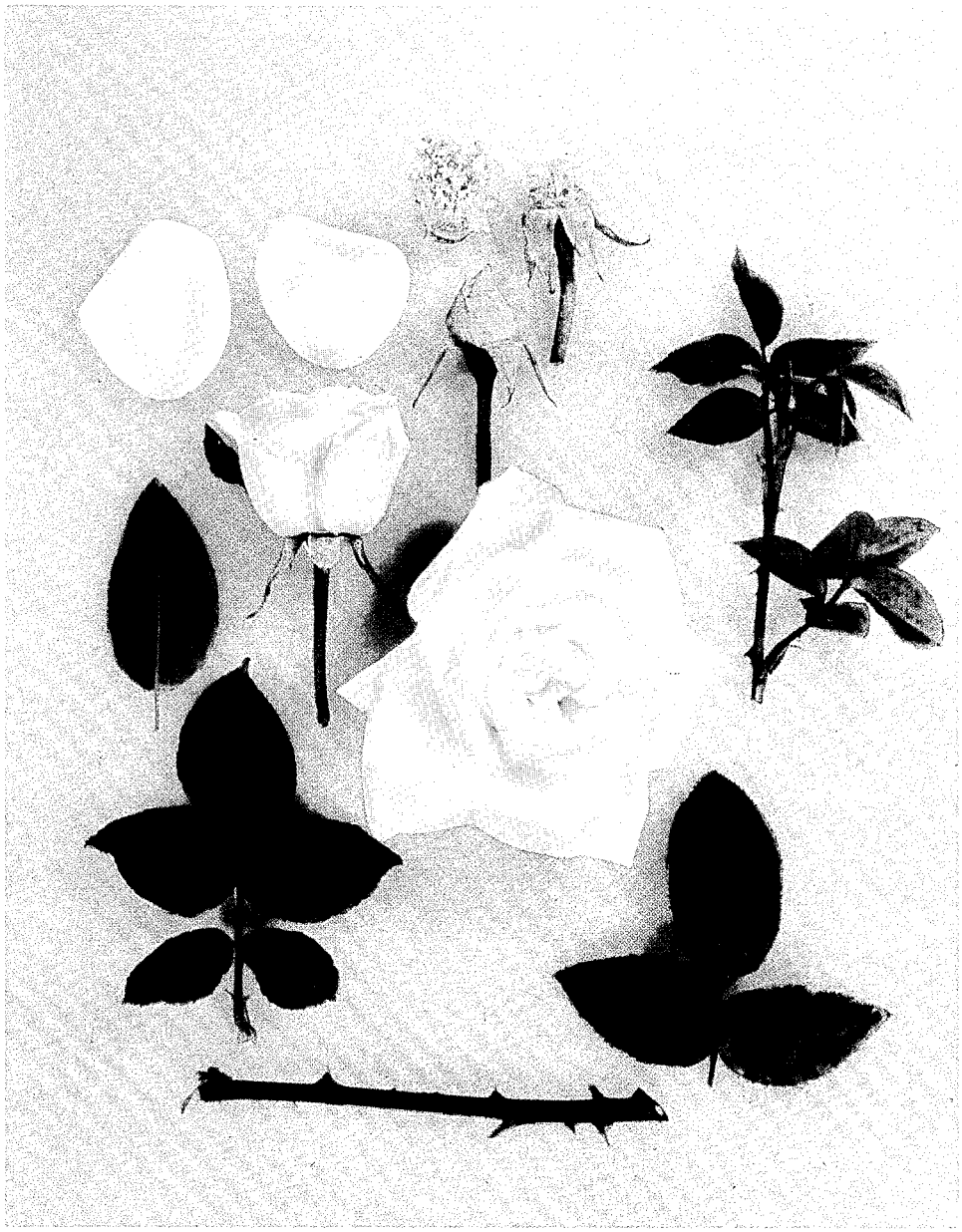
Inventor.
Carlos Camprubi
By: Robb & Robb
Attorneys.

United States Patent Office

Plant Pat. 2,055
Patented May 2, 1961

2,055

ROSE PLANT

Carlos Camprubi, Cornella de Llobregat (Barcelona), Spain, assignor to The Conard-Pyle Company, West Grove, Pa., a corporation of Pennsylvania Filed June 9, 1960, Ser. No. 35,100

1 Claim. (Cl. 47—61)

The present invention relates to a new and distinct variety of rose plant of the hybrid tea class, which was originated by me by crossing the variety "Alaska" (unpatented) with the variety "Virgo" (unpatented).

The primary objective of this breeding was to produce a new and improved white rose variety of the hybrid tea class which is characterized by a good bud form and double, well-formed blooms that are borne on a strong and vigorous plant. This objective was fully achieved, along with other desirable improvements, as evidenced by the following unique combination of characteristics which are outstanding in the new variety and which distinguish it from its parents, as well as from all other varieties of which I am aware:

(1) Good, well-branched and vigorous habits of growth;

(2) Excellent bud form;

(3) Double, well-formed blooms which do not show any tendency to "ball" in unfavorable weather conditions as is a common fault of white roses;

(4) Good substance of the flower petals; and (5) A pure white coloration of the flowers.

Asexual reproduction of my new variety by budding, as performed on my behalf at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; bush; greenhouse; outdoor; seedling; for cut flowers and for garden decoration.

Class: Hybrid tea.

Breeding: Seedling.

*Seed parent.*—"Alaska."

*Pollen parent.*—"Virgo."

Propagation: Holds its distinguishing characteristics through succeeding propagations by budding.

*Flower*

Locality where grown and observed: West Grove, Pennsylvania, U.S.A.

Flowers borne: Singly to stem; on stems of normal strength and medium length.

Quantity of bloom: Free, outdoors.

Continuity: Continuous.

Fragrance: From slight to moderate. Nature—tea.

Bud:

*Peduncle.*—Medium length; medium heaviness; erect; medium roughness; medium number of red-brown hairs. Color—from Fern Green, Plate 0862/3 to Pod Green, Plate 061.

*Before calyx breaks.*—Size—medium. Form—medium length; pointed; with a conspicuous neck; with slender, entire foliaceous parts extending beyond the tip of the bud equal to ¼ or less of its length.

*As calyx breaks.*—Color—Pea Green, Plate 61/2.

*As first petal opens.*—Size—medium. Form—medium length; ovoid. Color: outside—white, shading to Sap Green, Plate 62/3, with base of petal Pod Green, Plate 061/2, veined with Pod Green, Plate 061; inside—white at outer margin of petal, grading to Chartreuse Green, Plate 663/3, veined with Pod Green, Plate 061.

*Opening.*—Opens up well.

Bloom:

*Size (when fully open).*—Medium large; from 3¾ inches to 4¾ inches.

*Petalage.*—Double; from 55 to 65 petals; arranged irregularly.

*Form.*—Full and high-centered at first, but becoming cupped; petals being at first loosely rolled outward and remaining loosely rolled outward at maturity.

Petals: Leathery. Inside—satiny. Oustide—shiny. Shape: outer—round; intermediate—round; inner—lanceolate; irregular.

This description of a newly opened flower was made from a rose grown outdoors in the month of September at West Grove, Pennsylvania, U.S.A.:

*Color.*—Outer petal: outside surface—white, with base of petal Sap Green, Plate 62/3; inside surface—white, with base of petal Primrose Yellow, Plate 601/1. Intermediate petal: outside surface—white, with basal ¼ of petal Sap Green, Plate 62/3; inside surface—white, grading to Primrose Yellow, Plate 601/2. Inner petal: outside surface—Sap Green, Plate 62/3; inside surface—Sap Green, Plate 62/3, with base of petal Primrose Yellow, Plate 601/2.

This description was made from a rose that was open for three (3) days indoors in the month of September at West Grove, Pennsylvania, U.S.A.

*Color.*—Outer petal: outside surface—white, with base of petal Sap Green, Plate 62/3; inside surface—white, with base of petal Chartreuse Green, Plate 663/2. Inner petal: outside surface—white, with base of petal Sap Green, Plate 62/3; inside surface—white, with base of petal Primrose Yellow, Plate 601/2.

*General color effect.*—Newly opened flower—white. 3-days open—white.

*Behavior.*—Drop off cleanly.

*Flower longevity.*—On bush in garden—3 days in August. Cut roses grown outdoors and kept at living room temperatures—3 days in August.

*Reproductive organs*

Stamens: Many, arranged irregularly about pistils.

Filaments: Most with anthers; variable length. Color—Primrose Yellow, Plate 601/2.

Anthers: Medium size, all open at once; seldom an anther fused with a petaloid. Color—Chinese Yellow, Plate 606/1.

Pollen: Moderate abundance. Color—gold.

Pistils: Medium number.

Styles: Uneven; medium length; medium heaviness; bunched.

Stigma: Color—white yellow.

Ovaries: All enclosed in receptacle.
Hips: None observed.
Sepals: Permanent; medium length; spear-shaped.
Seeds: None observed.

*Plant*

Foliage:

*Leaves.*—Compound of 5 leaflets; abundant; moderately large; leathery.

*Leaflets.*—Shape—roundly oval, with apex acute. Base—obtuse. Margin—simply serrate.

*Color.*—Mature: upper surface—from Spinach Green, Plate 0960 to Ivy Green, Plate 0001060/3; under surface—Lavender Green, Plate 000761/1. Young: upper surface—Spinach Green, Plate 0960/2; under surface—between Willow Green, Plate 000862/2 and Willow Green, Plate 000862/1, lightly shaded with Oxblood Red, Plate 00823/3.

*Rachis (the supporting stem of the compound leaf).*—Medium caliper. Upper side—grooved; hairy. Under side—sparsely prickly.

*Stipules.*—Medium length; moderately narrow; with medium length points turning out at an angle of about 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Vigorous.

*Canes.*—Moderately heavy.

*Main stems.*—Dull. Color—Fern Green, Plate 0862. Prickles—several; color—Garnet Brown, Plate 00918/3. Hairs—none.

*Branches.*—Dull. Color—Willow Green, Plate 000862/1. Prickles—several; color—Erythrite Red, Plate 0027. Hairs—few; color—Erythrite Red, Plate 0027.

*New shoots.*—Dull. Color—Spinach Green, Plate 0960/3, lightly overlaid with Erythrite Red, Plate 0027/3. Prickles—several; color—Erythrite Red, Plate 0027/1 at base, with point Straw Yellow, Plate 604/1. Hairs—few; color—Erythrite Red, Plate 0027.

I claim:

A new and distinct variety of rose plant of the hybrid tea class, substantially as herein shown and described, characterized particularly as to novelty by the unique combination of good, well-branched and vigorous habits of growth, excellent bud form, double, well-formed blooms and the absence of any tendency thereof to "ball" under unfavorable weather conditions, good substance of the flower petals, and a pure white flower coloration.

No references cited.